US00PP16510P2

(12) United States Plant Patent
Gitzels

(10) Patent No.: US PP16,510 P2
(45) Date of Patent: May 9, 2006

(54) ***DAHLIA* PLANT NAMED 'BALDELSTREM'**

(50) Latin Name: *Dahlia variabilis*
Varietal Denomination: Baldelstrem

(75) Inventor: Jeroen Gitzels, Zwaag (NL)

(73) Assignee: Ball Horticultural Company, West Chicago, IL (US)

( * ) Notice: Subject to any disclaimer, the term of this patent is extended or adjusted under 35 U.S.C. 154(b) by 184 days.

(21) Appl. No.: 11/015,234

(22) Filed: Dec. 17, 2004

(51) Int. Cl.
*A01H 5/00* (2006.01)

(52) U.S. Cl. ..... Plt./321
(58) Field of Classification Search ..... Plt./321
See application file for complete search history.

*Primary Examiner*—Kent Bell
(74) *Attorney, Agent, or Firm*—Wood, Phillips, Katz, Clark & Mortimer

(57) ABSTRACT

A new and distinct *Dahlia* plant named 'Baldelstrem', characterized by its double pink-colored ray florets, yellow-colored disc florets, and vigorous, upright, and mounded growth habit.

2 Drawing Sheets

Latin name of genus and species of plant claimed: *Dahlia variabilis*.
Variety denomination: 'Baldelstrem'.

BACKGROUND OF THE INVENTION

The present invention relates to a new and distinct *Dahila* plant botanically known as *Dahlia variabilis* and hereinafter referred to by the cultivar name 'Baldelstrem'.

The new cultivar originated in a controlled breeding program in Enkhuizen, The Netherlands during July 1997. The objective of the breeding program was the development of freely flowering *Dahlia* cultivars with large inflorescences and an upright growth habit.

The female (seed) parent of the new cultivar was the proprietary breeding selection designated '97.1357', not patented, characterized by its very large size and long stems. The male (pollen) parent of the new cultivar was the cultivar Dapalipi, not patented, characterized by its compact growth habit and light pink-colored inflorescences. Seed from the above stated cross-pollination was germinated and grown to maturity. One plant within the progeny was discovered and selected by the inventor during May 1998 at Enkhuizen, The Netherlands.

Asexual reproduction of the new cultivar by terminal stem cuttings taken since May 1998 at Enkhuizen, The Netherlands and West Chicago, Ill. has demonstrated that the new cultivar reproduces true to type, with all characteristics as herein described, firmly fixed and retained through successive generations of such asexual propagation.

SUMMARY OF THE INVENTION

The new cultivar has not been observed under all possible environmental conditions to date. Accordingly, it is possible that the phenotype may vary somewhat with variations in the environment such as temperature, light intensity, and day length without, however, any variance in genotype.

The following characteristics of the new cultivar have been repeatedly observed and can be used to distinguish 'Baldelstrem' as a new and distinct cultivar of *Dahlia* plant:

1. Double pink-colored ray florets and yellow-colored disc florets.
2. Vigorous, upright, and mounded growth habit.

Plants of the new cultivar differ from plants of the female parent primarily in stem length and from the male parent primarily in inflorescence color and growth habit.

Of the many *Dahlia* cultivars known to the inventor, the most similar to the new cultivar is the cultivar Dapavio, U.S. Plant Pat. No. 11,492. However, in side by side comparisons, plants of the new cultivar differ from plants of 'Dapavio' in the following characteristics:

1. Plants of the new cultivar exhibit lighter ray floret color than do plants of 'Dapavio'.
2. Plants of the new cultivar exhibit larger inforescences than do plants of 'Dapavio'.

BRIEF DESCRIPTION OF THE PHOTOGRAPHS

The accompanying photographs show, as nearly true as it is reasonably possible to make the same in color illustrations of this type, typical inflorescence and foliage characteristics of the new cultivar. Colors in the photographs differ slightly from the color values cited in the detailed desciption, which accurately describes the colors of the new cultivar. The plants were grown for 11 weeks in a greenhouse at West Chicago, Ill.

DETAILED BOTANICAL DESCRIPTION

Figure 1:
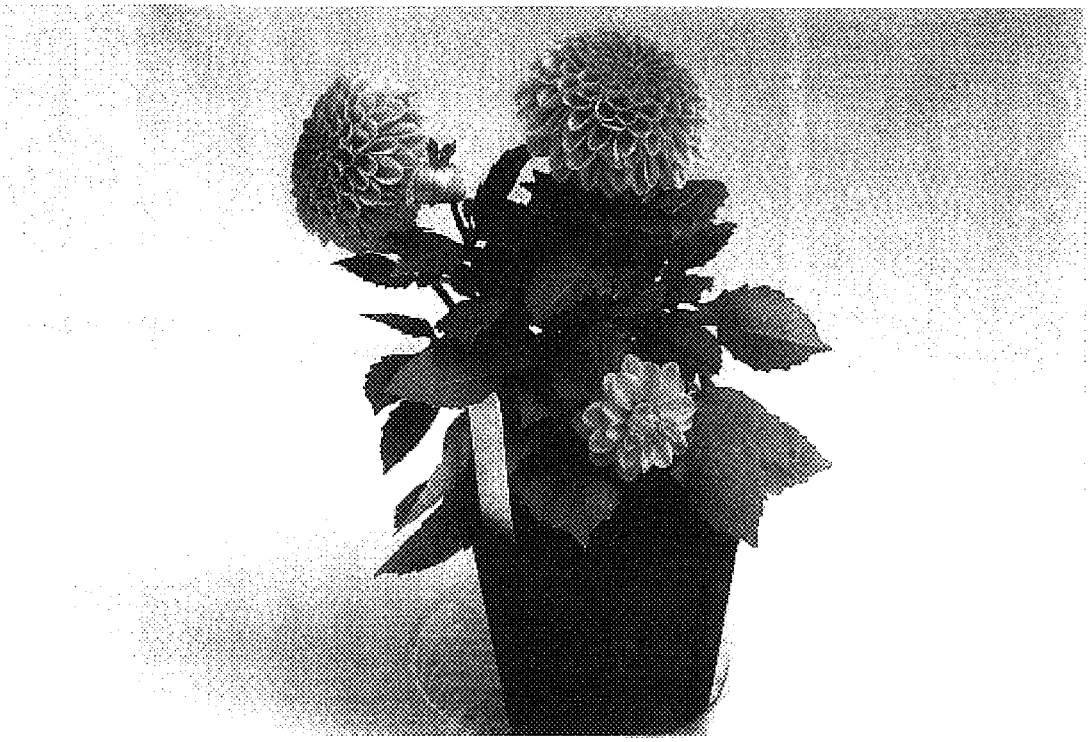
FIG. 1 illustrates a side view of the overall growth and flowering habit of 'Baldelstrem'.
Figure 2:
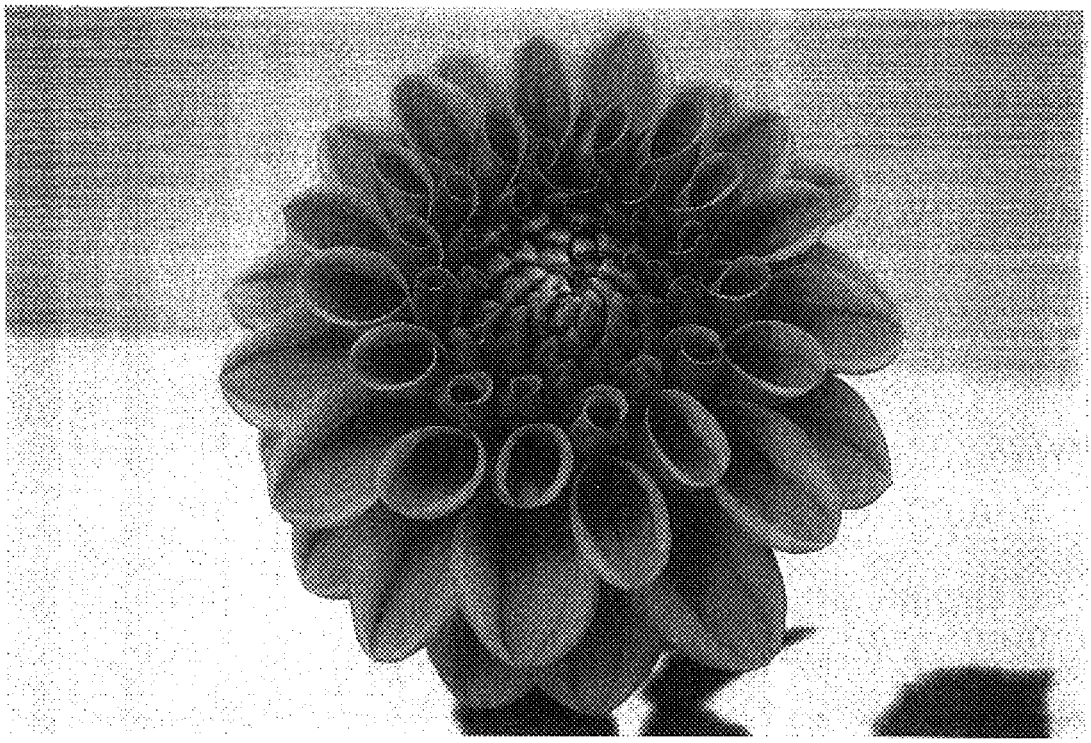
FIG. 2 illustrates a close-up view of a single inflorescence 'Baldelstrem' just opening.
Figure 3:
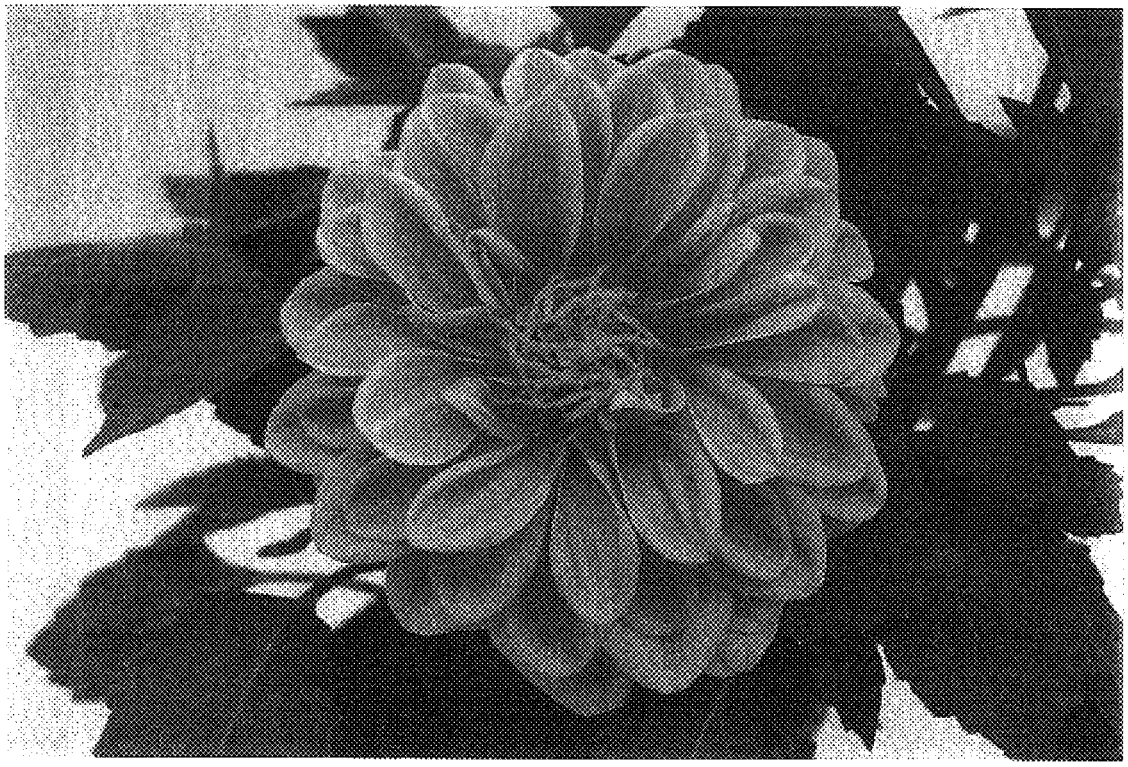
FIG. 3 illustrates a single fully open inflorescence of 'Baldelstrem'.

The chart used in the identification of colors described herein is the R.H.S. Colour Chart of The Royal Horticultural Society, London, England, 2001 edition, except where general color terms of ordinary significance are used. The color values were determined on Oct. 15, 2004 between 10:00 and 11:45 a.m. under natural light conditions in West Chicago, Ill.

The following descriptions and measurements describe plants produced from cuttings taken from stock plants and grown in a double polycarbonate-covered greenhouse in West Chicago, Ill. under conditions comparable to those used in commerical practice. The plants were grown in 10 cm pots for 11 weeks while utilizing a soilless growth medium. Greenhouse temperatures were maintained at approximately 65°–75° F. (18°–24° C.) during the day and approximately 60°–65° F. (15°–18° C.) during the night. Greenhouse light levels were maintained at approximately 4,000–6,000 footcandles during the day. Plants were pinched three weeks after planting of rooted cuttings.

Botanical classification: *Dahlia variabilis* cultivar Baldelstrem.

Parentage:

*Female parent.*—Proprietary *Dahlia* breeding selection designated '97.1357', not patened.

*Male parent.*—'Dapalipi', not patented.

Propagation:

*Type cutting.*—Terminal tip.

*Time to initiate roots.*—Approximately 7 to 10 days.

*Time to produce a rooted cutting.*—Approximately 21 to 28 days.

*Rooting habit.*—Freely branching.

*Root description.*—Fine, fibrous.

*Tubers.*—Will form under short day conditions of at least 13 to 14 hours of darkness.

Plant description:

*Crop time.*—Approximately 8–10 weeks.

*Growth habit.*—Basal branching, pinching enhances branching.

*General appearance and form.*—Upright, mounded, and vigorous.

*Size.*—Height from top of soil to top of plant plane: Approximately 25.6 cm. Width/area of spread: Approximately 22.4 cm.

*Branch description.*—Quantity per plant: Approximately 3. Strength: Strong. Length: Approximately 11.6 cm. Diameter: Approximately 6.2 mm. Length of center internode: Approximately 2.1 cm. Texture: Glabrous. Color: 143B with overlay of 183A at nodes.

*Foliage.*—Quantity of leaves per lateral branch: Approximately 13. Type: Compound. Quantity of leaflets per compound leaf: 3 or 5. Fragrance: None. Arrangement: Opposite. Aspect: At an acute angle to the stem. Leaflet: Shape: Ovate. Apex: Acute. Base: Attenuate. Margin: Dentate. Venation pattern: Pinnate. Length of mature trifoliate leaf: Approximately 5.4 cm. Width of mature trifoliate leaf: Approximately 6.6 cm. Length of petiole of mature trifoliate leaf: Approximately 2.1 cm. Diameter of petiole of mature trifoliate leaf: Approximately 1.9 mm. Texture of petiole of mature trifoliate leaf: Sparsely pubscent. Color of petiole of mature trifoliate leaf: 146C. Length of terminal leaflet: Approximately 4.6 cm. Width of terminal leaflet: Approximately 2.7 cm. Length of lateral leaflet: Approximately 3.4 cm. Width of lateral leaflet: Approximately 1.9 cm. Petiole of lateral leaflet: None. Texture of upper and lower surface of all leaflets: Moderately pubescent along veins only. Color of upper surface of mature foliage: Closest to 147A with venation of 144C. Color of lower surface of mature foliage: Closest to 147B with venation of 144C.

Flowering description:

*Outdoor flowering habit.*—'Baldelstrem' is freely flowering under outdoor growing conditions with substantially continuous blooming from spring through autumn and year round in greenhouse environment.

*Time to first flower.*—Approximately 8 weeks after the planting of a rooted cutting.

Inflorescence description:

*Appearance.*—Type: Composite. Form: Fully double, arising from leaf axils on strong peduncles, positioned just over the foliage. Disc and ray florets arranged acropetally on a capitulum. Persistent.

*Quantity per plant.*—Approximately 3 fully open at any one time.

*Lastingness of bloom.*—Approximately 4 weeks from first open ray floret to senescence.

*Shape/size.*—Hemispherical. Diameter: Approximately 7.6 cm. Depth: Approximately 4.4 cm. Disc diameter: Approximately 1 cm. Receptacle diameter: Approximately 9 mm. Receptacle height/depth: Approximately 3 mm. Receptacle color: 144C.

*Flower bud.*—Rate of opening: Approximately 2 weeks from first color to full bloom. Quantity showing color per plant: Approximately 2. Quantity per plant: Approximately 2 showing color at any one time. Shape: Ovate. Length at first color: Approximately 3 cm. Width at first color: Approximately 1.7 cm. Texture: Glabrous.

*Fragrance.*—None.

*Ray florets.*—Quantity: Approximately 53 per inforescence arranged in several overlapping whorls.Shape: Ellitptic. Apex: Emarginate. Base: Attenuate, fused to form tube. Margin: Entire. Length: Approximately 2.4 cm. Width: Approximately 1.1 cm. Texture: Glabrous. Color of upper surface when first open: 69A with 13B at base. Color of lower surface when first open: 69B. Color of upper surface when fully opened: 73A with venation of 67C and area at base of 67A. Color of lower surface when fully opened: 73D with venation of 67D.

*Disc florets.*—Quantity: Approximately 27. Shape: Elongated, cylindrical. Apex: 5 acute tips. Length: 1.2 cm. Diameter at apex: Approximately 3 mm. Diameter at base: Approximately 1 mm. Texture: Glabrous. Color: Transparent, 9A at apex, 150D at base.

*Peduncle.*—Strength: Strong. Aspect: Erect. Length: Approximately 5.6 cm. Diameter: Approximately 1.5 mm. Texture: Glabrous. Color: 146B.

*Phyllaries.*—Quantity: One per floret. Shape: Lanceolate. Apex: Emarginate. Base: Truncate. Margin: Entire. Length: 8 mm. Width: 5 mm. Texture: Glabrous, papery. Color: Transparent, 150C at apex, 150D at base.

*Secondary phyllaries.*—Quantity: Approximately 8. Shape: Lanceolate. Apex: Acute. Base: Attenuate. Margin: Entire. Length: Approximately 9 mm. Width: Approximately 4 mm. Texture: Glabrous. Color of upper and lower surface: 144A.

*Reproductive organs.*—Andoecium — On disc florets. Stamen number: 4. Anther shape: Linear. Anther length: Approximately 3 mm. Anther color: 164A. Pollen amount: Abundant. Pollen color: 17A. Gynoecium—On disc and ray florets. Pistil. Pistil length: Approximately 1.3 cm. Stigma length: 2.5 mm. Stigma color: 20A. Style length: 5.5 mm. Style color: 145D. Ovary length: 3 mm. Ovary color: 145C.

Seed and fruit production: Neither seed nor fruit production has been observed.

Disease and pest resistance: Resistance to pathogens and pests common to *Dahlia* has not been observed.

What is claimed is:

1. A new and distinct cultivar of *Dahlia* plant named 'Baldelstrem', substantially as herein shown and described.

* * * * *